United States Patent
Matsuura et al.

(10) Patent No.: US 9,481,625 B2
(45) Date of Patent: Nov. 1, 2016

(54) PROCESS FOR PRODUCING CYCLOHEXANONE COMPOUND

(71) Applicant: Mitsui Chemicals, Inc., Minato-ku, Tokyo (JP)

(72) Inventors: Akira Matsuura, Higashiosaka (JP); Takuro Watanabe, Kishiwada (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/779,918

(22) PCT Filed: Apr. 1, 2014

(86) PCT No.: PCT/JP2014/059646
§ 371 (c)(1),
(2) Date: Sep. 24, 2015

(87) PCT Pub. No.: WO2014/163080
PCT Pub. Date: Oct. 9, 2014

(65) Prior Publication Data
US 2016/0046553 A1    Feb. 18, 2016

(30) Foreign Application Priority Data
Apr. 5, 2013    (JP) .................. 2013-079802

(51) Int. Cl.
| | |
|---|---|
| *C07C 45/00* | (2006.01) |
| *B01J 23/44* | (2006.01) |
| *B01J 21/04* | (2006.01) |
| *B01J 23/58* | (2006.01) |
| *B01J 35/10* | (2006.01) |
| *B01J 37/02* | (2006.01) |
| *B01J 31/02* | (2006.01) |
| *C07D 223/10* | (2006.01) |

(52) U.S. Cl.
CPC .............. *C07C 45/006* (2013.01); *B01J 21/04* (2013.01); *B01J 23/44* (2013.01); *B01J 23/58* (2013.01); *B01J 31/0237* (2013.01); *B01J 31/0244* (2013.01); *B01J 35/1014* (2013.01); *B01J 35/1019* (2013.01); *B01J 35/1038* (2013.01); *B01J 35/1061* (2013.01); *B01J 35/1066* (2013.01); *B01J 37/0201* (2013.01); *C07C 45/00* (2013.01); *C07D 223/10* (2013.01)

(58) Field of Classification Search
CPC ....... C07C 45/006; B01J 21/04; B01J 23/44; B01J 23/58
USPC ......................................................... 568/338
See application file for complete search history.

(56) References Cited

U.S. PATENT DOCUMENTS

| | | | |
|---|---|---|---|
| 2,891,096 A * | 6/1959 | Clingman | ............. C07C 403/24 546/184 |
| 3,076,810 A | 2/1963 | Duggan et al. | |
| 3,305,586 A | 2/1967 | Phielix | |
| 4,203,923 A | 5/1980 | Yeh et al. | |
| 4,918,239 A | 4/1990 | Wang et al. | |
| 5,395,976 A | 3/1995 | Scharschmidt et al. | |
| 6,046,365 A | 4/2000 | Kiel | |

FOREIGN PATENT DOCUMENTS

| | | |
|---|---|---|
| GB | 1063357 | 3/1967 |
| GB | 1563044 | 3/1980 |
| JP | S62-144749 A | 6/1987 |
| JP | H04-013644 A | 1/1992 |
| JP | H11-035513 A | 2/1992 |
| JP | H06-199714 A | 7/1994 |
| JP | 2002-226459 A | 8/2002 |
| JP | 2007-204407 A | 8/2007 |
| WO | WO2008/056768 A1 * | 5/2008 .............. B01J 31/28 |

OTHER PUBLICATIONS

International Search Report issued in International Patent Application No. PCT/JP2014/059646 mailed Jul. 1, 2014.
Office Action issued in Japanese Patent Application No. 2015-510097 mailed Aug. 23, 2016.

* cited by examiner

*Primary Examiner* — Sikarl Witherspoon
(74) *Attorney, Agent, or Firm* — Foley & Lardner LLP

(57) ABSTRACT

The invention has an object of providing an economical and highly efficient process for producing a cyclohexanone compound such as cyclohexanone. An aspect of the invention resides in a process for producing a cyclohexanone compound by performing hydrogenation reaction of a phenol compound in a gas phase in the presence of a palladium catalyst supported on a carrier to produce the corresponding cyclohexanone compound, wherein the hydrogenation reaction is carried out in the presence of at least one nitrogen compound selected from ammonia, amine compounds and heteroaromatic compounds.

11 Claims, 1 Drawing Sheet

PROCESS FOR PRODUCING CYCLOHEXANONE COMPOUND

TECHNICAL FIELD

The present invention relates to an efficient process for producing a cyclohexanone compound by the hydrogenation reaction of a phenol compound in a gas phase.

BACKGROUND ART

As known in the art, the hydrogenation reaction of phenol in the presence of a palladium catalyst gives a mixture including cyclohexanone and cyclohexanol (Patent Literatures 1 and 2). Cyclohexanone is used as a raw material in the production of caprolactam, and cyclohexanol mixed in the cyclohexanone is an undesired impurity. For example, cyclohexanol may be converted into cyclohexanone by dehydrogenation with a copper oxide/zinc oxide catalyst (Patent Literature 3). However, additional costs are incurred in order to separate a cyclohexanone/cyclohexanol mixture obtained by the hydrogenation reaction of phenol into cyclohexanone (boiling point 156.4° C.) and cyclohexanol (boiling point 161.1° C.) and also to dehydrogenate cyclohexanol. In consideration of these costs, the occurrence of cyclohexanol as a byproduct in the hydrogenation reaction of phenol is desirably suppressed to the minimum.

Because cyclohexanol is formed by the hydrogenation reaction of cyclohexanone, the amount of byproduct cyclohexanol may be reduced by decreasing the rate of the conversion of phenol. However, cyclohexanone and phenol, and cyclohexanol and phenol form maximum-boiling azeotropes and therefore decreasing the conversion rate gives rise to another economic problem that a significantly high cost is incurred to separate cyclohexanone and cyclohexanol as the products from the unreacted phenol. Thus, phenol is desirably converted at as high a conversion rate as possible.

Further, the hydrogenation reaction of phenol produces high-boiling byproducts based on cyclohexylcyclohexanone, in addition to cyclohexanol. These byproducts are generally difficult to convert to cyclohexanone by an affordable method in contrast to the dehydrogenation of cyclohexanol into cyclohexanone. Thus, an increase in the amount of cyclohexylcyclohexanone byproduct leads to a decrease in the yield of cyclohexanone, resulting in poor economic efficiency.

From an industrial viewpoint, the satisfaction of both high phenol conversion rate and high cyclohexanone selectivity is an important key to the economically advantageous production of cyclohexanone. The production of cyclohexanone by the hydrogenation reaction of phenol in a gas phase is generally performed by passing a mixture gas of phenol and hydrogen through a palladium catalyst supported on an alumina carrier. The process, however, is not applicable to an industrial scale because the catalyst is frequently deactivated in a short time.

To address the above problem, for example, it is reported that a palladium catalyst which is supported on a carrier prepared by mixing alumina with an alkaline earth metal hydroxide is less prone to deactivation and shows enhanced cyclohexanone selectivity as compared to when γ-alumina is used as the carrier (Patent Literature 4). However, the carrier made by this method has a defect in that mechanical strength is generally low. Further, the hydrogenation reaction of phenol involves a large excess of hydrogen and the catalytic activity is below the level required for use on an industrial scale.

To avoid this problem, the use of alumina spinel as a carrier is reported (Patent Literature 5). This approach realizes high mechanical strength and sustained catalytic activity. However, this method entails more complicated carrier production steps and involves more expensive raw materials than when usual alumina is used. These facts inevitably raise the carrier production cost.

From the viewpoints described above, the development of a low-cost and simple process which can produce cyclohexanone with a high yield is desired.

CITATION LIST

Patent Literature

Patent Literature 1: U.S. Pat. No. 3,305,586
Patent Literature 2: U.S. Pat. No. 3,076,810
Patent Literature 3: U.S. Pat. No. 4,918,239
Patent Literature 4: GB1063357
Patent Literature 5: U.S. Pat. No. 5,395,976

SUMMARY OF INVENTION

Technical Problem

In light of the problems in the art discussed above, an object of the invention is to provide an economical and highly efficient process for producing a cyclohexanone compound such as cyclohexanone.

Solution to Problem

In order to achieve the above object, the present inventors carried out extensive studies on the production of a cyclohexanone compound such as cyclohexanone by the gas-phase hydrogenation reaction of a phenol compound such as phenol using a palladium catalyst supported on a carrier. As a result, the present inventors have found that the presence of a specific nitrogen compound in the hydrogenation reaction enhances the catalytic activity, suppresses the formation of byproducts to improve the selectivity for the cyclohexanone compound such as cyclohexanone, and retards the decrease in catalytic activity. The present invention has been completed based on the finding.

Specifically, the invention includes the following aspects.

[1] A process for producing a cyclohexanone compound by performing hydrogenation reaction of a phenol compound in a gas phase in the presence of a palladium catalyst supported on a carrier to produce the corresponding cyclohexanone compound, wherein the hydrogenation reaction is carried out in the presence of at least one nitrogen compound selected from ammonia, amine compounds and heteroaromatic compounds.

[2] A process for producing cyclohexanone by performing hydrogenation reaction of phenol in a gas phase in the presence of a palladium catalyst supported on a carrier to produce the cyclohexanone, wherein the hydrogenation reaction is carried out in the presence of at least one nitrogen compound selected from ammonia, amine compounds and heteroaromatic compounds.

[3] The process for producing cyclohexanone described in [2], wherein the nitrogen compound is free from a structure formed by the bonding of a hydrogen atom to a nitrogen atom.

[4] The process for producing cyclohexanone described in [3], wherein the nitrogen compound is an amine compound having a tertiary amine structure.

[5] The process for producing cyclohexanone described in [4], wherein the nitrogen compound is composed solely of hydrogen, carbon and nitrogen atoms.

[6] The process for producing cyclohexanone described in any of [2] to [5], wherein the nitrogen compound is the nitrogen compound attached to the surface of the catalyst as a result of a contact with the palladium catalyst before the hydrogenation reaction.

[7] The process for producing cyclohexanone described in any of [2] to [5], wherein the nitrogen compound is the nitrogen compound added together with the raw material phenol.

[8] The process for producing cyclohexanone described in [7], wherein the amount of the supply of the nitrogen compound is 0.005 to 0.05 wt % relative to the amount of the feed of phenol taken as 100 wt %.

[9] The process for producing cyclohexanone described in [7], wherein the amount of the supply of the nitrogen compound is 0.01 to 0.05 wt % relative to the amount of the feed of phenol taken as 100 wt %.

[10] The process for producing cyclohexanone described in any of [2] to [9], wherein the carrier is porous alumina.

[11] The process for producing cyclohexanone described in any of [2] to [10], wherein the palladium catalyst supported on the carrier further includes at least one metal element selected from lithium, sodium, potassium, magnesium, calcium and barium.

[12] The process for producing cyclohexanone described in any of [2] to [11], wherein the reaction is performed in the presence of water.

[13] A process for producing caprolactam, wherein the process uses cyclohexanone produced by the production process described in any of [2] to [12].

[14] A catalyst obtained by bringing at least one nitrogen compound selected from ammonia, amine compounds and heteroaromatic compounds into contact with a palladium catalyst supported on a carrier so as to attach the nitrogen compound to the surface of the catalyst.

Advantageous Effects of Invention

The process for producing a cyclohexanone compound according to the present invention is excellent in particular in terms of production cost, and the target cyclohexanone compound may be produced while achieving process advantages and economic advantages.

Further, the process for producing cyclohexanone according to the present invention has the following effects and is excellent in particular in terms of production cost. Thus, target cyclohexanone may be produced with process advantages and economic advantages.

(1) The amount of cyclohexanol formed as a byproduct is reduced. Because the load required to separate cyclohexanone and cyclohexanol is reduced, the purification cost may be saved. Further, the dehydrogenation of cyclohexanol to recover cyclohexanone is feasible with a smaller dehydrogenation unit.

(2) The amount of high-boiling byproducts is reduced, and thereby the basic unit of cyclohexanone may be enhanced.

(3) The catalytic activity is enhanced to make it possible to reduce the amounts of hydrogen and the catalyst that are used. Thus, the hydrogenation reactor may be reduced in size, and the catalyst cost may be saved.

(4) The decrease in catalytic activity with time may be retarded. Consequently, the catalyst regeneration cycles may be extended and the loss of production during the regeneration periods may be reduced.

DESCRIPTION OF EMBODIMENTS

Figure 1:
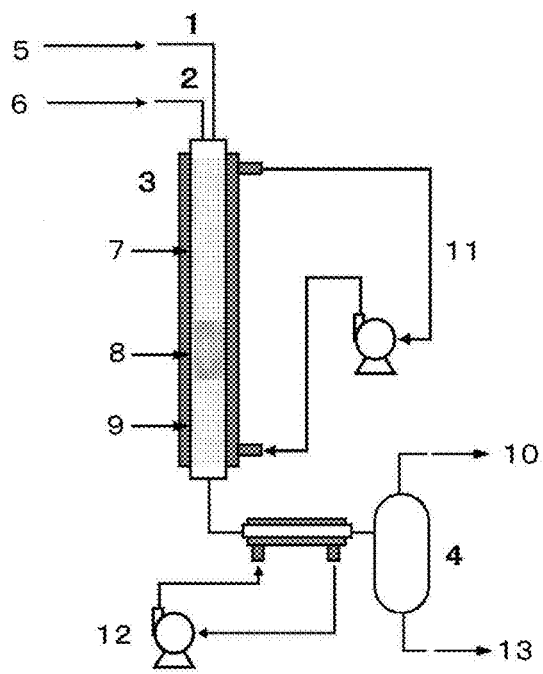
FIG. 1 is a schematic view illustrating a reaction apparatus used in Examples of the invention.

In a process for producing a cyclohexanone compound according to the invention, the hydrogenation reaction of a phenol compound is performed in a gas phase in the presence of a palladium catalyst supported on a carrier to produce the corresponding cyclohexanone compound. The process is characterized in that the hydrogenation reaction is carried out in the presence of at least one nitrogen compound selected from ammonia, amine compounds and heteroaromatic compounds. Details of the process will be described below.

Examples of the phenol compounds used in the invention include phenol, cresol, butylphenol, other monoalkylphenols, and dialkylphenols. Phenol compounds having 6 to 12 carbon atoms in the molecule are preferable.

In the cyclohexanone compound production process of the invention, the phenol compound is hydrogenated to give the corresponding cyclohexanone compound. The term "corresponding cyclohexanone compound" means that the benzene ring of the phenol compound used as the raw material is hydrogenated into the cyclohexane ring and the C—OH structure in the phenol compound is converted to the carbonyl (C=O). When phenol is used as the phenol compound, the corresponding cyclohexanone compound is cyclohexanone. When the phenol compound is cresol, the corresponding cyclohexanone compound is methylcyclohexanone.

In the cyclohexanone compound production process of the invention, it is preferable that the phenol compound is phenol and the cyclohexanone compound is cyclohexanone.

That is, the cyclohexanone compound production process of the invention is preferably a process for producing cyclohexanone. In the process for producing cyclohexanone according to the invention, the hydrogenation reaction of phenol is performed in a gas phase in the presence of a palladium catalyst supported on a carrier to produce cyclohexanone. The process is characterized in that the hydrogenation reaction is carried out in the presence of at least one nitrogen compound selected from ammonia, amine compounds and heteroaromatic compounds.

Hereinbelow, details will be described with respect to the process for producing cyclohexanone.

(Catalysts)

In the invention, the hydrogenation reaction is catalyzed by a palladium catalyst supported on a carrier. (In the following description, the catalyst is sometimes written simply as the "supported palladium catalyst".)

The carrier is not particularly limited as long as the carrier is inert in the hydrogenation reaction. Examples include metal oxides such as silica, alumina, silica-alumina, magnesia, titania and zirconia. Of these, alumina is preferable, and porous alumina is particularly preferable. The average pore diameter of the porous alumina is preferably 10 to 500 nm. The average pore volume per unit weight of the porous alumina is preferably about 0.2 to 3 ml/g. The specific surface area per unit weight of the porous alumina is preferably about 10 to 200 m$^2$/g.

Metallic palladium may be supported on the carrier by any known method without limitation. For example, metallic palladium may be supported by impregnating the carrier with an aqueous solution of a palladium compound such as sodium tetrachloropalladate (II) and bringing the impregnated carrier into contact with a reductant such as hydrazine. The proportion of the palladium supported on the carrier in 100 parts by weight of the catalyst is usually in the range of 0.1 to 10.0 parts by weight, and preferably 0.1 to 3.0 parts by weight.

The shape of the supported palladium catalyst is not particularly limited and may be any of various shapes such as spheres, pellets, extrudates and irregularly shaped fragments. Spheres are particularly preferable. In the case of the spherical catalyst, the average particle diameter is usually in the range of 1 to 10 mm, and preferably 2 to 5 mm.

In the supported palladium catalyst, a compound(s) of an alkali metal and/or an alkaline earth metal may be further supported. That is, the supported palladium catalyst may further include a compound(s) of an alkali metal and/or an alkaline earth metal, more specifically, may further include at least one metal element selected from lithium, sodium, potassium, magnesium, calcium and barium.

The compound(s) of an alkali metal and/or an alkaline earth metal may be supported on the supported palladium catalyst by a known method. For example, the metals may be supported on the catalyst by impregnating the supported palladium catalyst still free from any alkali metal and/or alkaline earth metal compounds with an aqueous solution of any of compounds such as hydroxides, nitrate salts, acetate salts and carbonate salts of metals such as lithium, sodium, potassium, magnesium, calcium and barium, followed by drying or calcination. The proportion of the alkali metal and/or the alkaline earth metal supported on the catalyst in 100 parts by weight of the whole catalyst is usually in the range of 0.1 to 10.0 parts by weight, and preferably 0.2 to 5.0 parts by weight. The compounds of alkali metals and alkaline earth metals may be used singly, or two or more may be used in combination.

(Nitrogen Compounds)

In the invention, the gas-phase hydrogenation reaction of phenol is performed in the presence of the supported palladium catalyst and also in the presence of at least one nitrogen compound selected from ammonia, amine compounds and heteroaromatic compounds. While the compounds of alkali metals and/or alkaline earth metals that are conventionally used in the production of cyclohexanone are necessarily supported on catalysts when they are used, the nitrogen compound in the present application does not require a carrier and the use thereof is a simple method capable of controlling the acidity on the surface of the catalyst.

In the invention, the "at least one nitrogen compound selected from ammonia, amine compounds and heteroaromatic compounds" is also written simply as the "nitrogen compound".

The nitrogen compounds may be used singly, or two or more may be used in combination.

The nitrogen compound is a compound having a nitrogen atom in the molecule and is at least one compound selected from ammonia, amine compounds and heteroaromatic compounds.

The amine compound is a substance which has a structure resulting from the substitution of a hydrogen atom in ammonia with a hydrocarbon group. The heteroaromatic compound is an aromatic heterocyclic compound.

The nitrogen compound is preferably free from a structure formed by the bonding of a hydrogen atom to a nitrogen atom. When the nitrogen compound free from a structure formed by the bonding of a hydrogen atom to a nitrogen atom, the amount of high-boiling compounds formed as byproducts tends to be advantageously reduced.

Examples of the nitrogen compounds free from a structure formed by the bonding of a hydrogen atom to a nitrogen atom include tertiary amines (A) which have one or more amine structures in the molecule and all the amine structures have a tertiary amine structure, and pyridine. Examples of the nitrogen compounds that have a structure formed by the bonding of a hydrogen atom to a nitrogen atom include ammonia and amines having a primary amine structure or a secondary amine structure in the molecule.

It is desirable that the nitrogen compound be as inert as possible to phenol, hydrogen, and cyclohexanone and cyclohexanol as the products under reaction conditions. From this viewpoint, the nitrogen compound free from a structure formed by the bonding of a hydrogen atom to a nitrogen atom is preferable. The reasons as to why the use of the nitrogen compound free from a structure formed by the bonding of a hydrogen atom to a nitrogen atom is preferable will be described in detail below. The present inventors assume that the nitrogen compound free from a structure formed by the bonding of a hydrogen atom to a nitrogen atom are the true compounds that contribute to the enhancements in reaction results such as phenol conversion rate and cyclohexanone selectivity. The nitrogen compound having a hydrogen-nitrogen bond in its molecule probably undergoes dehydration condensation with cyclohexanone as a raw material under reaction conditions adopted in the present invention, forming an imine or an enamine as an intermediate product. These intermediates are hydrogenated under the reaction conditions and are finally converted to nitrogen compounds free from a structure formed by the bonding of a hydrogen atom to a nitrogen atom. The present inventors assume that the advantageous effects in the hydrogenation reaction of the invention are achieved as a result of the above mechanism. Because, however, part of cyclohexanone that is the desired product is consumed by the dehydration condensation with the nitrogen compound having a hydrogen-nitrogen bond, the cyclohexanone selectivity is lowered. Thus, the nitrogen compound having a hydrogen-nitrogen bond and the nitrogen compound free from a structure formed by the bonding of a hydrogen atom to a nitrogen atom may be used as the same when only an enhancement in phenol conversion rate is desired. When, however, not only the phenol conversion rate but also the cyclohexanone selectivity are to be enhanced, it is preferable to use the nitrogen compound free from a structure formed by the bonding of a hydrogen atom to a nitrogen atom.

The nitrogen compound is preferably an amine compound having a tertiary amine structure. The tertiary amine structure is advantageous in that it tends to exhibit a strong interaction with an acid site of the carrier in the supported palladium catalyst.

The nitrogen compound is preferably composed solely of hydrogen, carbon and nitrogen atoms. If atoms other than hydrogen, carbon and nitrogen atoms are present, the compound may be decomposed during the reaction to form impurities. For this reason, the nitrogen compounds composed solely of hydrogen, carbon and nitrogen atoms are preferable.

Specific examples of the nitrogen compounds include ammonia, trimethylamine, triethylamine, triisopropylamine, tributylamine, trioctylamine, N,N-dimethylaniline, N,N-dimethylbenzylamine, N,N,N',N'-tetramethylethylenediamine, N,N,N',N'',N''-pentamethyldiethylenetriamine, N-methylpiperidine, N-methylmorpholine, N,N'-dimethylpiperazine, quinuclidine, 1,4-diazabicyclo[2.2.2]octane, hexamethylenetetramine, N,N-dimethylaminopyridine, 1,5-diazabicyclo[4.3.0]-5-nonene, 1,8-diazabicyclo[5.4.0]-7-undecene, pyridine, quinoline, pyrazine, triazine, N,N,N',N'-tetramethylguanidine, diethylaminopropylamine, imidazole, methylamine, ethylamine, n-propylamine, isopropylamine, n-butylamine, n-pentylamine, isoamylamine, cyclohexylamine, aniline, toluidine, ethylenediamine, diethylenetriamine, triethylenetetramine, tetraethylenepentamine, propylenediamine, N-methylpropylamine, N-methyl-n-butylamine, N-methyldodecylamine, N-methyl-n-octadecylamine, N-ethyl-n-butylamine, N-ethyldodecylamine, N-ethyl-n-octadecylamine, piperidine, piperazine and morpholine.

Of these nitrogen compounds, those nitrogen compounds free from a structure formed by the bonding of a hydrogen atom to a nitrogen atom are preferable, with examples including trimethylamine, triethylamine, triisopropylamine, tributylamine, trioctylamine, N,N-dimethylaniline, N,N-dimethylbenzylamine, N,N,N',N'-tetramethylethylenediamine, N,N,N',N'',N''-pentamethyldiethylenetriamine, N-methylpiperidine, N-methylmorpholine, N,N'-dimethylpiperazine, quinuclidine, 1,4-diazabicyclo[2.2.2]octane, hexamethylenetetramine, N,N-dimethylaminopyridine, 1,5-diazabicyclo[4.3.0]-5-nonene, 1,8-diazabicyclo[5.4.0]-7-undecene, pyridine, quinoline, pyrazine and triazine.

Of these nitrogen compounds free from a structure formed by the bonding of a hydrogen atom to a nitrogen atom, amine compounds having a tertiary amine structure are preferable, with examples including trimethylamine, triethylamine, triisopropylamine, tributylamine, trioctylamine, N,N-dimethylaniline, N,N-dimethylbenzylamine, N,N,N',N'-tetramethylethylenediamine, N,N,N',N'',N''-pentamethyldiethylenetriamine, N-methylpiperidine, N-methylmorpholine, N,N'-dimethylpiperazine, quinuclidine, 1,4-diazabicyclo[2.2.2]octane, hexamethylenetetramine, N,N-dimethylaminopyridine, 1,5-diazabicyclo[4.3.0]-5-nonene and 1,8-diazabicyclo[5.4.0]-7-undecene.

Of these amine compounds with a tertiary amine structure and free from a structure formed by the bonding of a hydrogen atom to a nitrogen atom, those compounds composed solely of hydrogen, carbon and nitrogen atoms are preferable, with examples including trimethylamine, triethylamine, triisopropylamine, tributylamine, trioctylamine, N,N-dimethylaniline, N,N-dimethylbenzylamine, N,N,N', N'-tetramethylethylenediamine, N,N,N',N'',N''-pentamethyldiethylenetriamine, N-methylpiperidine, N,N'-dimethylpiperazine, quinuclidine, 1,4-diazabicyclo[2.2.2]octane, hexamethylenetetramine, N,N-dimethylaminopyridine, 1,5-diazabicyclo[4.3.0]-5-nonene and 1,8-diazabicyclo[5.4.0]-7-undecene.

From the point of view that the removal from target cyclohexanone is easy, the nitrogen compound used in the invention is preferably an amine having a widely different boiling point from cyclohexanone. An amine compound having 1 to 3 nitrogen atoms in the molecule is preferable, and an amine compound having one nitrogen atom in the molecule is more preferable.

The molecular weight of the nitrogen compound used in the invention is preferably 50 to 500, and more preferably 50 to 400 because an amine having a widely different boiling point from cyclohexanone may be easily removed from target cyclohexanone.

From the point of view that the removal from target cyclohexanone is easy, trimethylamine, triethylamine, triisopropylamine, tributylamine and trioctylamine are particularly preferably used as the nitrogen compounds in the invention.

A desired nitrogen compound is an amine having a widely different boiling point from cyclohexanone because it may be easily removed from target cyclohexanone by a general distillation operation. In the case where separation by distillation is difficult, other removal methods such as adsorption may be adopted.

In the production process of the invention, the hydrogenation reaction is performed in the presence of the nitrogen compound described above. The nitrogen compound may be the nitrogen compound added together with the raw material phenol or may be the nitrogen compound attached to the surface of the catalyst as a result of a contact with the palladium catalyst before the hydrogenation reaction. Preferably, the nitrogen compound is the nitrogen compound attached to the surface of the catalyst as a result of a contact with the palladium catalyst before the hydrogenation reaction.

The nitrogen compound may be involved in the reaction system together with the supported palladium catalyst by any method without limitation. The following three methods are main examples which may be selected appropriately in accordance with characteristics such as the boiling point and the solubility in solvents of the nitrogen compound used. These methods may be used singly, or two or more may be used in combination.

(1) The supported palladium catalyst that has been contacted with the liquid nitrogen compound is used as the catalyst in the hydrogenation reaction of phenol: When the nitrogen compound is in a liquid form, the nitrogen compound may be used in the contact as such without a solvent; and when the nitrogen compound is viscous liquid or solid, the compound may be appropriately used in the form of a solution in a solvent.

The liquid amine is preferably brought into contact with the catalyst by impregnating the catalyst with the liquid amine by a batchwise operation, or by continuously passing the liquid amine through the catalyst packed in a fixed bed reactor. After the contact, the catalyst is separated from the liquid amine and may be dried using an appropriate method such as nitrogen gas flow, vacuum or heating.

Although the nitrogen compound may be used in any amount without limitation, the amount is preferably 0.5 to 10 times by weight the amount of the catalyst. If the amount is below this range, the nitrogen compound may not have a sufficient contact with the catalyst and may fail to improve the catalyst performance sufficiently. The contact time is usually in the range of 1 minute to 10 hours, and preferably in the range of 10 minutes to 5 hours. The treatment temperature is usually in the range of 0 to 200° C., and preferably in the range of 20 to 100° C.

(2) The supported palladium catalyst that has been contacted with the gaseous nitrogen compound is used as the catalyst in the hydrogenation reaction of phenol. The gaseous amine is preferably brought into contact with the supported palladium catalyst by vaporizing the nitrogen compound by heating the compound to or above its boiling point under operation conditions, and passing the gas through the catalyst packed in a fixed bed reactor. In this method, the gaseous amine may be supplied together with an inert gas such as, for example, nitrogen, methane or ethane.

Although the nitrogen compound may be used in any amount without limitation, the amount is preferably 0.1 to 10 times by weight the amount of the catalyst. The contact time is usually in the range of 1 minute to 10 hours, and preferably in the range of 10 minutes to 5 hours. The treatment temperature is not particularly limited as long as the nitrogen compound used is in the gaseous state, but is usually in the range of 0 to 300° C., and preferably in the range of 50 to 200° C.

In the methods (1) and (2), the nitrogen compound is brought into contact with the supported palladium catalyst. The resultant catalyst has the nitrogen compound attached to the surface of the supported palladium catalyst.

(3) The nitrogen compound is continuously supplied to the reactor while concurrently performing the hydrogenation reaction of phenol. In this case, the nitrogen compound is desirably gas under the hydrogenation reaction conditions. The nitrogen compound may be supplied to the reactor individually or as a solution in the raw material phenol. When the nitrogen compound is supplied individually to the reactor, the supply may take place in the absence of solvents or the compound may be supplied as a solution in an appropriate solvent. Although the nitrogen compound may be supplied in any amount without limitation, the amount is preferably in the range of 0.005 to 10 wt %, more preferably in the range of 0.005 to 0.05 wt %, and still more preferably in the range of 0.01 to 0.05 wt % relative to the amount of the feed of phenol taken as 100 wt %. If the amount is below this range, the compound may fail to improve the catalyst performance sufficiently. If the amount exceeds the above range, the cost incurred to separate the nitrogen compound from cyclohexanone produced may be increased.

(Hydrogenation Reaction)

In the cyclohexanone production process of the invention, the hydrogenation reaction is performed in a gas phase usually by supplying a gas mixture of phenol and hydrogen to the reactor in the presence of the supported palladium catalyst and the nitrogen compound.

In the invention, the hydrogenation reaction of phenol is usually performed at a temperature in the range of 100° C. to 300° C., and preferably in the range of 150 to 250° C. At an excessively low reaction temperature, the reaction rate may be decreased. If, on the other hand, the reaction temperature is excessively high, undesired side reactions may take place to cause problems such as a decrease in cyclohexanone selectivity and a decrease in catalytic activity due to the buildup of high-boiling byproducts on the catalyst.

The molar ratio of hydrogen used in the reaction to phenol is usually in the range of 2 to 10, more preferably in the range of 2.5 to 8, and still more preferably 3.0 to 5.0 relative to 1 mol of phenol.

The amount of the supported palladium catalyst used in the invention is not particularly limited. For example, the quotient of the amount (weight) of supply per hour of the raw material (phenol) divided by the weight of the catalyst (the weight of the supported palladium catalyst), namely WHSV, is preferably in the range of 0.01 to 10 $h^{-1}$, and more preferably in the range of 0.05 to 5.0 $h^{-1}$.

Hydrogen may contain gases which are inert in the reaction, for example, methane, ethane and nitrogen. On the other hand, the contents of gases such as carbon dioxide and carbon monoxide are preferably as low as possible because these gases may impair the catalytic activity.

The reaction pressure is usually in the range of 0.08 to 0.8 MPaA. In view of the fact that the mixture of raw material phenol and hydrogen is to be supplied to the reactor as a gas and also in consideration of other factors such as the pressure resistance of the reaction apparatus, it is preferable that the pressure be set to normal pressure to 0.3 MPaA.

The reaction is carried out in a gas phase, and therefore does not necessarily involve a solvent. However, a solvent may be used as required for purposes of, for example, facilitating the handling of phenol by mixing phenol with a solvent during the raw material supply step to decrease the solidification temperature of phenol, or decreasing the gasification temperature of the mixture of phenol and hydrogen. In particular, those solvents which exhibit high solubility for phenol and do not inhibit the reaction and the purification in a later stage are preferable, with examples including hydrocarbon compounds such as cyclohexane, benzene and toluene. The solvents may be used singly, or two or more may be used in combination.

In the production process of the invention, the reaction may be performed in the presence of water. When the reaction involves water, the water may be water attached to the surface of the catalyst as a result of a contact of the palladium catalyst with water before the hydrogenation reaction. Alternatively, water may be supplied in addition to phenol and hydrogen.

The contact of the catalyst with water, and the contact of the catalyst with the nitrogen compound may take place at the same time. In this case, for example, the simultaneous contacts of the catalyst with water and of the catalyst with the nitrogen compound may be attained by subjecting an aqueous solution of the nitrogen compound or an aqueous dispersion of the nitrogen compound to the aforementioned method (1) or (2) for involving the nitrogen compound in the reaction system. In this case, the nitrogen compound and water are usually used in such amounts that the proportion of the nitrogen compound is in the range of 0.1 to 50 wt % relative to the total of the nitrogen compound and water taken as 100 wt %.

When water is supplied in addition to phenol and hydrogen, the amount of the supply of water is 10% or less, and preferably 0.5 to 2.0 wt % or below relative to the amount of the feed of phenol taken as 100 wt %.

The state of water is not particularly limited, and water may be supplied as a liquid or a gas. Preferably, water is supplied in the form of a gas, namely, as water vapor.

Supplying water is advantageous in that the phenol conversion rate tends to be enhanced.

Cyclohexanone that is the target product in the production process of the invention may be separated from the reaction liquid by known methods such as distillation, extraction and adsorption. The unreacted raw material and the solvent may be recovered and recycled to the reaction system.

(Reaction Apparatuses)

Because the hydrogenation reaction of phenol is highly exothermic, the reaction heat needs to be continuously removed with the progress of the reaction. Because of this fact and in view of the characteristic that the reaction in the invention is performed on the fixed bed catalyst in a gas phase, it is preferable to use a multitubular reactor that is a combination of a heat exchanger and a reactor, or a radial flow reactor.

Cyclohexanone obtained by the production process of the invention may be used in various applications in which cyclohexanone has been conventionally used. Because the production process of the invention is economical and highly efficient, the cyclohexanone obtained is preferably used for the production of, for example, caprolactam. That is, the process for producing caprolactam according to the present invention is characterized in that the process uses cyclohexanone produced by the cyclohexanone production process described hereinabove.

EXAMPLES

The present invention will be described in detail based on examples and comparative examples hereinbelow. However, the scope of the invention is not limited to such examples.

(Continuous Cyclohexanone Synthesis Reaction)

With a reaction apparatus illustrated in FIG. 1, the hydrogenation reaction of phenol was performed in the following manner. The reaction apparatus shown in FIG. 1 had a facility including supply pipes 1 and 2, a fixed bed reactor 3 filled with a catalyst, and a gas-liquid separation tank 4. The reactor 3 was continuously supplied with hydrogen or nitrogen 5 from the supply pipe 1, and with phenol or an amine 6 from the supply pipe 2. The phenol and the amine were supplied with use of a pump.

The fixed bed reactor was a SUS 316 reaction tube 18 mm in outer diameter, 15 mm in inner diameter and 600 mm in length (a thermometer well 3.18 mm in outer diameter) which was fitted with a jacket (a SUS 304 oil jacket 18.4 mm in inner diameter and 600 mm in length) containing a silicone oil as a heating medium 11. The reaction product was condensed by being cooled with a cooling medium 12 in a heat exchanger disposed at the outlet of the reactor. A vent gas 10 such as excess hydrogen was separated, and the reaction product 13 was sampled. The components present in the reaction liquid (the reaction product) were quantitatively determined by gas chromatography analysis with respect to the reaction liquid, and the phenol conversion rate and the selectivities for the components were calculated.

(Gas Chromatography (GC) Analysis)

Chromatograph: GC-2010 (manufactured by Shimadzu Corporation)

Capillary column: TC-WAX (manufactured by GL Science, inner diameter 0.32 mm×length 60 m)

Carrier gas: nitrogen (1.4 mL/min)

Measurement temperature conditions: The temperature was increased from 100° C. at 5° C./min. After reaching 240° C., the temperature was kept constant for 12 minutes and the measurement was completed.

Inlet temperature: 240° C.

FID detector temperature: 240° C.

Amount of injection: 1.0 μL (Quantitative Determination of Components Present in Reaction Liquid)

By an absolute calibration method, GC calibration curves were prepared beforehand with respect to phenol, cyclohexanone, cyclohexanol, cyclohexylcyclohexanone, cyclohexane and benzene. With reference to the information obtained, the results of the GC measurement were analyzed by a common procedure to quantitatively determine the contents of the components present in the reaction liquid.

Example 1

The reaction tube was loaded with 4.0 g of 0.5 wt % palladium alumina pellets (HD-101 manufactured by N.E. CHEMCAT CORPORATION), thereby forming a catalyst-packed layer 8. Glass beads having a diameter of 2 to 4 mm were placed on the upper side and the lower side of the catalyst-packed layer in amounts of 60 g and 15 g, respectively (catalyst-packed layers 7 and 9). SUS meshes were interposed at the boundaries to avoid mixing of the beads with the catalyst.

The catalyst was pretreated with an amine by passing triethylamine at 0.5 mL/min and nitrogen at 150 mL/min in the downward direction from the top to the bottom of the reaction tube while the temperature of the oil in the jacket was set at 180° C. The triethylamine was supplied to the catalyst-packed layer as a gas by being vaporized in the preheating layer that was composed of the glass beads disposed on the upper side of the catalyst-packed layer. The supply of triethylamine was terminated after 5 minutes, and nitrogen was supplied for another 1 hour. The pretreatment operation was thus completed.

Figure 2:
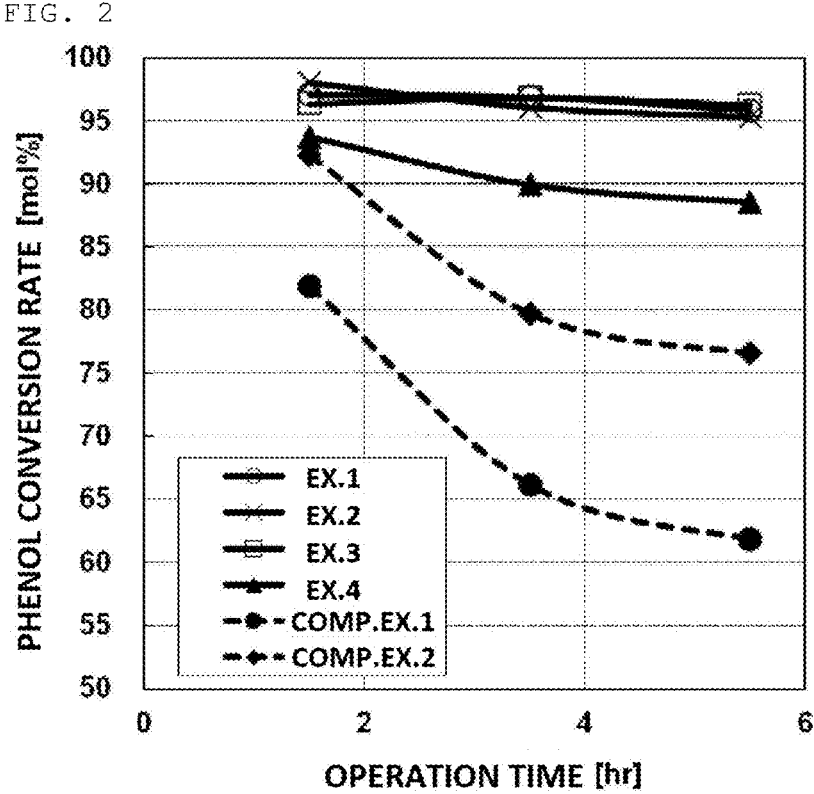
FIG. 2 is a diagram plotting changes with time in the phenol conversion rate after the lapse of 1.5 hours, 3.5 hours and 5.5 hours during the hydrogenation reaction in Inventive Examples and Comparative Examples.

The hydrogenation reaction of phenol was performed by passing hydrogen at 4.3 NL/hr and phenol at 6.0 g/hr (the hydrogen/phenol molar ratio was 4, and the WHSV was 1.5 $h^{-1}$) in the downward direction from the top to the bottom of the reaction tube. The phenol was supplied to the catalyst-packed layer in the form of a gas by being vaporized in the preheating layer. The temperature of the oil in the jacket was adjusted so that the hotspot temperature in the catalyst layer would be 180° C. In this process, the pressure at the inlet and the outlet of the reaction tube was 0.00 MPaG. The reaction liquid was analyzed by gas chromatography to quantitatively determine the components present in the reaction liquid, and the phenol conversion rate and the selectivities for the components were calculated. The changes with time in the phenol conversion rate are described in Table 1 and FIG. 2. Further, Table 2 describes the phenol conversion rate and the selectivities for the components after 1.5 hours of the supply of phenol.

Example 2

The hydrogenation reaction of phenol was performed in the same manner as in Example 1, except that the amine was changed to diethylamine. The changes with time in the phenol conversion rate are described in Table 1 and FIG. 2. Further, Table 2 describes the phenol conversion rate and the selectivities for the components after 1.5 hours of the supply of phenol.

Example 3

The hydrogenation reaction of phenol was performed in the same manner as in Example 1, except that the amine was changed to n-butylamine. The changes with time in the phenol conversion rate are described in Table 1 and FIG. 2. Further, Table 2 describes the phenol conversion rate and the selectivities for the components after 1.5 hours of the supply of phenol.

Example 4

The hydrogenation reaction of phenol was performed in the same manner as in Example 1, except that the amine was changed to pyridine. The changes with time in the phenol conversion rate are described in Table 1 and FIG. 2. Further, Table 2 describes the phenol conversion rate and the selectivities for the components after 1.5 hours of the supply of phenol.

Comparative Example 1

The hydrogenation reaction of phenol was performed in the same manner as in Example 1, except that the pretreatment with the amine was omitted. The changes with time in the phenol conversion rate are described in Table 1 and FIG. 2.

Comparative Example 2

The hydrogenation reaction of phenol was performed in the same manner as in Comparative Example 1, except that the hydrogen supply rate was changed to 2.9 NL/hr and the phenol supply rate was changed to 4.0 g/hr (hydrogen/phenol molar ratio=4, WHSV=1.0 $h^{-1}$). The changes with time in the phenol conversion rate are described in Table 1 and FIG. 2. Further, Table 2 describes the phenol conversion rate and the selectivities for the components after 1.5 hours of the supply of phenol.

TABLE 1

Changes in phenol conversion rate

|  |  | Ex. 1 | Ex. 2 | Ex. 3 | Ex. 4 | Comp. Ex. 1 | Comp. Ex. 2 |
|---|---|---|---|---|---|---|---|
| Amine |  | Triethylamine | Diethylamine | N-butylamine | Pyridine | None | None |
| Phenol conversion rate [mol %] | After 1.5 hr | 97.1 | 98.0 | 96.4 | 93.8 | 82.0 | 92.3 |
|  | After 5.5 hr | 95.9 | 95.3 | 96.3 | 88.6 | 61.8 | 76.6 |

TABLE 2

Phenol conversion rate and selectivities after 1.5 hours

|  |  | Ex. 1 | Ex. 2 | Ex. 3 | Ex. 4 | Comp. Ex. 2 |
|---|---|---|---|---|---|---|
| Amine |  | Triethylamine | Diethylamine | N-butylamine | Pyridine | None |
| Phenol conversion rate [mol %] |  | 97.1 | 98.0 | 96.4 | 93.8 | 92.3 |
| Selectivities 1) | Cyclohexanone | 91.2 | 92.9 | 93.5 | 92.9 | 87.5 |
|  | Cyclohexanol | 5.81 | 4.23 | 3.04 | 2.67 | 3.89 |
|  | Cyclohexylcyclohexanone | 2.30 | 2.27 | 2.62 | 3.74 | 7.39 |
|  | Cyclohexane and benzene | 0.40 | 0.33 | 0.27 | 0.24 | 0.35 |
|  | Other components | 0.29 | 0.27 | 0.57 | 0.45 | 0.87 |

1) The selectivities for cyclohexanone, cyclohexanol, cyclohexylcyclohexanone, cyclohexane and benzene indicate mol % values determined from the concentrations calculated based on the GC calibration curves. The selectivity for "other components" observed in the high-boiling region on the GC chart was calculated assuming that the molar response factor relative to cyclohexylcyclohexanone was 1.

Example 5

The hydrogenation reaction of phenol was performed in the same manner as in Example 1, except that 4.0 g of the 0.5 wt % palladium alumina pellets were replaced by 5.0 g of 0.5 wt % potassium-0.5 wt % palladium alumina pellets. Table 3 describes the phenol conversion rate and the selectivities for the components after 11 hours of the supply of phenol.

Example 6

The hydrogenation reaction of phenol was performed in the same manner as in Example 1, except that the 0.5 wt % palladium alumina pellets were replaced by 0.5 wt % potassium-0.5 wt % palladium alumina pellets and the triethylamine was replaced by a 30 wt % aqueous trimethylamine solution. Table 3 describes the phenol conversion rate and the selectivities for the components after 3.5 hours of the supply of phenol.

TABLE 3

Phenol conversion rate and selectivities

|  |  | Ex. 5 | Ex. 6 |
|---|---|---|---|
|  | Amine | Triethylamine | 30 wt % aqueous trimethylamine solution |
| Phenol conversion rate [mol %] |  | 98.0 | 99.4 |
| Selectivities 1) | Cyclohexanone | 97.6 | 96.0 |
|  | Cyclohexanol | 1.98 | 2.77 |
|  | Cyclohexylcyclohexanone | 0.36 | 1.26 |
|  | Cyclohexane and benzene | 0.02 | 0.02 |
|  | Other components | 0.00 | 0.00 |

1) The selectivities for cyclohexanone, cyclohexanol, cyclohexylcyclohexanone, cyclohexane and benzene indicate mol % values determined from the concentrations calculated based on the GC calibration curves. The selectivity for "other components" observed in the high-boiling region on the GC chart was calculated assuming that the molar response factor relative to cyclohexylcyclohexanone was 1.

REFERENCE SIGNS LIST

1 . . . SUPPLY PIPE
2 . . . SUPPLY PIPE
3 . . . REACTOR
4 . . . GAS-LIQUID SEPARATOR
5 . . . HYDROGEN OR NITROGEN
6 . . . PHENOL OR AMINE
7 . . . GLASS BEAD LAYER
8 . . . CATALYST-PACKED LAYER
9 . . . GLASS BEAD LAYER
10 . . . VENT GAS
11 . . . HEATING MEDIUM
12 . . . COOLING MEDIUM
13 . . . REACTION PRODUCT (REACTION LIQUID)

The invention claimed is:

1. A process for producing a cyclohexanone compound by performing hydrogenation reaction of a phenol compound in a gas phase in the presence of a palladium catalyst supported on a carrier to produce the corresponding cyclohexanone compound, wherein the hydrogenation reaction is carried out in the presence of at least one nitrogen compound selected from ammonia, amine compounds and heteroaromatic compounds, wherein the nitrogen compound is free from a structure formed by the bonding of a hydrogen atom to a nitrogen atom, wherein the palladium catalyst supported on the carrier further includes at least one metal element selected from lithium, sodium, potassium, magnesium, calcium and barium, and wherein the palladium catalyst supported on the carrier is obtained by impregnating the supported palladium catalyst still free from any alkali metal and/or alkaline earth metal compounds with an aqueous solution of hydroxides, nitrate salts, acetate salts or carbonate salts of at least one metal element selected from lithium, sodium, potassium, magnesium, calcium or barium, followed by drying or calcination.

2. A process for producing cyclohexanone by performing hydrogenation reaction of phenol in a gas phase in the presence of a palladium catalyst supported on a carrier to produce the cyclohexanone, wherein the hydrogenation reaction is carried out in the presence of at least one nitrogen compound selected from ammonia, amine compounds and heteroaromatic compounds, wherein the nitrogen compound is free from a structure formed by the bonding of a hydrogen atom to a nitrogen atom, wherein the palladium catalyst supported on the carrier further includes at least one metal element selected from lithium, sodium, potassium, magnesium, calcium and barium, and wherein the palladium catalyst supported on the carrier is obtained by impregnating the supported palladium catalyst still free from any alkali metal and/or alkaline earth metal compounds with an aqueous solution of hydroxides, nitrate salts, acetate salts or carbonate salts of at least one metal element selected from lithium, sodium, potassium, magnesium, calcium or barium, followed by drying or calcination.

3. The process for producing cyclohexanone according to claim 2, wherein the nitrogen compound is an amine compound having a tertiary amine structure.

4. The process for producing cyclohexanone according to claim 3, wherein the nitrogen compound is composed solely of hydrogen, carbon and nitrogen atoms.

5. The process for producing cyclohexanone according to claim 2, wherein the nitrogen compound is the nitrogen compound attached to the surface of the catalyst as a result of a contact with the palladium catalyst before the hydrogenation reaction.

6. The process for producing cyclohexanone according to claim 2, wherein the nitrogen compound is the nitrogen compound added together with the raw material phenol.

7. The process for producing cyclohexanone according to claim 6, wherein the amount of the supply of the nitrogen compound is 0.005 to 0.05 wt % relative to the amount of the feed of phenol taken as 100 wt %.

8. The process for producing cyclohexanone according to claim 6, wherein the amount of the supply of the nitrogen compound is 0.01 to 0.05 wt % relative to the amount of the feed of phenol taken as 100 wt %.

9. The process for producing cyclohexanone according to claim 2, wherein the carrier is porous alumina.

10. The process for producing cyclohexanone according to claim 2, wherein the reaction is performed in the presence of water.

11. A process for producing caprolactam, wherein the process uses cyclohexanone produced by the production process described in claim 2.

* * * * *